United States Patent
Love

(10) Patent No.: US 6,494,904 B1
(45) Date of Patent: Dec. 17, 2002

(54) METHOD AND APPARATUS FOR FORMING VASCULAR PROSTHESES

(75) Inventor: Charles S. Love, Santa Barbara, CA (US)

(73) Assignee: Ramus Medical Technologies, Santa Barbara, CA (US)

( * ) Notice: Subject to any disclaimer, the term of this patent is extended or adjusted under 35 U.S.C. 154(b) by 0 days.

(21) Appl. No.: 09/091,942

(22) PCT Filed: Dec. 27, 1996

(86) PCT No.: PCT/US96/20868

§ 371 (c)(1),
(2), (4) Date: Dec. 18, 1998

(87) PCT Pub. No.: WO97/24081

PCT Pub. Date: Jul. 10, 1997

(51) Int. Cl.$^7$ ................................................. A61F 2/06
(52) U.S. Cl. ............................................... 623/1.1
(58) Field of Search .................. 128/334; 623/1.13, 623/1.22, 1.32, 1.16, 1.1, 1.11

(56) References Cited

U.S. PATENT DOCUMENTS

| | | |
|---|---|---|
| 3,408,659 A | 11/1968 | Thiele et al. |
| 3,514,791 A | 6/1970 | Sparks |
| 3,562,820 A | 2/1971 | Braun |
| 3,894,530 A | 7/1975 | Dardik et al. |
| 3,974,526 A | 8/1976 | Dardik et al. |
| 3,988,782 A | 11/1976 | Dardik et al. |
| 4,300,244 A | 11/1981 | Bokros |
| 4,502,159 A | 3/1985 | Woodroof et al. |
| 4,539,716 A | 9/1985 | Bell |
| 4,666,442 A | 5/1987 | Arru et al. |
| 4,728,328 A | 3/1988 | Hughes et al. |
| 4,731,073 A * | 3/1988 | Robinson ................ 623/1 |
| 4,798,606 A | 1/1989 | Pinchuk |
| 4,801,299 A | 1/1989 | Brendel et al. |
| 4,820,298 A | 4/1989 | Leveen et al. |
| 4,822,361 A | 4/1989 | Okita et al. |
| 4,842,575 A | 6/1989 | Hoffman, Jr. et al. |
| 5,131,908 A | 7/1992 | Dardik et al. |
| 5,163,955 A | 11/1992 | Love et al. |
| 5,192,311 A | 3/1993 | King et al. |

(List continued on next page.)

FOREIGN PATENT DOCUMENTS

| | | |
|---|---|---|
| WO | WO 90/14804 | 12/1990 |
| WO | WO 94/04099 | 3/1994 |
| WO | WO 95/16410 | 6/1995 |
| WO | WO 95/16411 | 6/1995 |
| WO | WO 95/16412 | 6/1995 |
| WO | WO 95 25547 | 9/1995 |
| WO | WO 97/09006 | 3/1997 |

OTHER PUBLICATIONS

Sako, Y. "Prevention of Dilation in Autogenous Venous and Pericardial Grafts In the Thoracic Aorta," (1951) *Surgery*, 30:148–160.

*Primary Examiner*—Eduardo C. Robert
(74) *Attorney, Agent, or Firm*—Townsend and Townsend and Crew LLP

(57) ABSTRACT

A vascular prosthesis (10) comprises pericardial, fascial, or other tissue (12) formed over a tubular support frame. A first exemplary tubular support frame comprises an inner helical member (16) and an outer helical member (14), where the tissue is rolled and captured therebetween. A second exemplary tubular support frame (60, 62) comprises a plurality of ring elements (64, 72) which are located alternately on the outside and on the inside of the rolled tissue. Other exemplary frames employ fasteners (84, 98) for penetrating the rolled tissue and attaching tissue to frame elements. The tissue is preferably obtained from the patient who is to receive the vascular prosthesis, with the tissue being mounted over the frame immediately prior to use.

4 Claims, 9 Drawing Sheets

U.S. PATENT DOCUMENTS

| | | |
|---|---|---|
| 5,215,541 A | 6/1993 | Nashef et al. |
| 5,297,564 A | 3/1994 | Love |
| 5,326,370 A | 7/1994 | Love et al. |
| 5,326,371 A | 7/1994 | Love et al. |
| 5,372,821 A | 12/1994 | Badylak et al. |
| 5,423,885 A | 6/1995 | Williams |
| 5,423,887 A | 6/1995 | Love et al. |
| 5,425,741 A | 6/1995 | Lemp et al. |
| 5,464,450 A * | 11/1995 | Buscemi et al. ............... 623/6 |
| 5,556,414 A | 9/1996 | Turi |
| 5,607,466 A * | 3/1997 | Imbert et al. ............... 623/1.11 |
| 5,800,524 A * | 9/1998 | Borghi ........................... 623/1 |
| 5,865,723 A * | 2/1999 | Love ........................... 600/36 |

\* cited by examiner

METHOD AND APPARATUS FOR FORMING VASCULAR PROSTHESES

BACKGROUND OF THE INVENTION

1. Field of the Invention

The present invention relates generally to medical methods and devices, and more particularly to a method and apparatus for forming vascular prostheses from host tissue sources.

Coronary and peripheral atherosclerosis are characterized by partial or total occlusion of the arteries resulting from the accumulation of lipids, smooth muscle cells, connective tissue, and glycosaminoglycans on the arterial wall. Atherosclerosis of the coronary arteries is a particular problem and can cause angina and myocardial infarction (heart attack). Although many coronary lesions can be treated with percutaneous techniques, such as angioplasty and atherectomy, more tortuous and severely diseased arteries frequently require surgical intervention and bypass, commonly referred to as coronary artery bypass graft (CABG) surgery.

CABG surgery relies on the surgical attachment of a vascular graft to bypass the arterial occlusion in order to restore blood flow to the coronary vasculature. The nature of the vascular graft can have a significant impact on the ultimate success of the procedure. A preferred vascular graft is formed from autologous internal mammary artery (IMA), where the resulting grafts have a patency rate approaching 95% ten years following the procedure. The use of IMA grafts, however, is limited by their length, and the need to harvest the artery from the patient can result in post-surgical complications. The autologous saphenous vein is a second common source for vascular grafts. While generally available in the necessary lengths, the saphenous vein is not ideally suited for replacement as an arterial vessel, and patency rates at ten years are often below 50%. Moreover, removal of the saphenous vein from the leg can also cause post-surgical complications.

Because of the limitations on autologous vascular sources, a variety of synthetic and non-autologous biological prostheses have been proposed. Common synthetic prostheses are formed from Dacron® and PTFE, and can perform well when employed in larger diameters, i.e., above 6 mm. Smaller synthetic prostheses, however, occlude at a relatively high rate. Non-autologous biological conduits which have been utilized as vascular prostheses include human umbilical vein grafts and bovine internal mammary arteries. Synthetic grafts have also been seeded with human and other mammalian cells or proteins, e.g., collagens, in an effort to improve their long-term patency rate. Presently, however, none of these approaches has demonstrated long-term patency, particularly in smaller diameter grafts.

Of particular interest to the present invention, preparation of vascular prostheses from autologous pericardium has been proposed. Pericardial tissue is harvested from the patient and formed into a tubular graft by suturing along a longitudinal line. While promising, the use of sutures can result in an irregular seam which, in turn, can cause turbulent blood flow and result in clot formation. Moreover, such grafts are unsupported and subject to kinking and collapse. The grafts further lack an inherently round geometry and are subject to dimensional changes, e.g., elongation and aneurysmal formation. Because of the dimensional uncertainty, it is difficult to match such grafts to the precise dimensional requirements of the particular application, e.g, caliber and length. The suturing of vascular prostheses from pericardium is labor intensive and time consuming, and the resulting structures are subject to rupture and other structural failure. Thus, the outcome of using sutured pericardial tissue grafts is uncertain at best.

For these reasons, it would be desirable to provide improved vascular prostheses for use in CABG and other procedures. Such prostheses should be biocompatible with the patient, resistant to kinking and collapse, and easy to implant. Moreover, the prostheses should be non-thrombogenic, resistant to infection, and easy to sterilize and store. It would be particularly desirable to provide improved methods and apparatus for preparing vascular prostheses from autologous tissue sources, where the prostheses can be prepared in a range of diameters and lengths, and can be readily assembled in the operating room after the tissue has been harvested. In particular, the vascular prostheses should be readily assemblable, preferably without suturing, in a manner that allows precise and uniform dimensions and preferably be available in a kit form to facilitate assembly.

2. Description of the Background Art

U.S. Pat. No. 4,502,159, describes a vascular prosthesis made by suturing glutaraldehyde-treated pericardial tissue along a longitudinal seam. SU 1217362 (Abstract) describes reinforcing arteries by securing pericardial tissue over the artery. U.S. Pat. No. 3,562,820, describes forming tissue-containing prostheses over removable mandrels. The use of glutaraldehyde and other agents for treating tissue and prosthetic devices to reduce antigenicity is described in U.S. Pat. Nos. 3,988,782; 4,801,299; 5,215,541, and Brazilian applications 89/03621 and 90/03762. U.S. Pat. No. 4,539,716, describes the fabrication of an artificial blood vessel from collagen and other natural materials. U.S. Pat. Nos. 3,894,530 and 3,974,526, describe the formation of vascular prostheses from the arteries or veins present in the umbilical cord. U.S. Pat. No. 5,372,821, describes the use of tissue for forming artificial ligament grafts for use in orthopedic procedures. U.S. Pat. No. 3,408,659, describes the preparation of vascular artificial prostheses from other body lumens. French application FR 2,714,816, (Abstract) discloses a helically supported vascular prosthesis. A number of medical literature publications describe the use of vascular prostheses formed form tissue. See, for example, Rendina et al. (1995) *J. Thorac. Cardiovasc. Surg.* 110:867–868; Hvass et al. (1987) *La Presse Médicale* 16:441–443; Allen and Cole (1977) *J. Ped. Surg.* 12:287–294; and Sako (1951) *Surgery* 30:148–160. Other patents and published applications relating to synthetic vascular grafts include U.S. Pat. Nos. 4,728,328; 4,731,073; 4,798,606; 4,820,298; 4,822,361; and 4,842,575; and PCT publications WO 94/22505 and WO 95/25547. Patents and published applications relating to kits for preparing replacement heart valves from pericardial and other autologous tissue sources are described in U.S. Pat. Nos. 5,163,955; 5,297,564; 5,326,370; 5,326,371; 5,423,887; and 5,425,741.

SUMMARY OF THE INVENTION

The present invention provides improved vascular prostheses and methods for their preparation. The vascular prostheses are formed in part from animal tissue, usually autologous tissue from the patient receiving the prostheses, which is supported on a separate support frame. Typically, the tissue is pericardial, fascial, rectus sheath, venous tissue, or other tissue harvested from the patient immediately before the CABG or other implantation procedure. After harvesting, the tissue is usually but not necessarily treated in a stabilizing medium, such as a cross-linking agent, and then attached to the frame in the operating room. The frame precisely defines the length and dimensions of the vascular graft and inhibits kinking and collapse of the graft after implantation. Preferably, the tissue will be tolled or otherwise formed over the frame so that adjacent longitudinal edges are overlapped to seal the resulting lumen of the graft and prevent blood leakage. In this way, suturing of the graft can be avoided.

Such vascular prostheses have a number of advantages. When using autologous tissue, the grafts are biocompatible and non-immunogenic. The grafts are durable, and use of the separate frame provides dimensional stability and inhibits unintended dilation, rupture, elongation, and kinking. Moreover, the vascular prosthesis may be prepared in a range of diameters and lengths, with the tissue sources providing a relatively unlimited source of prosthetic material. The vascular prostheses are relatively easy to fabricate, with attachment of the tissue to the frame being readily performable in an operating room environment. The frame components of the graft are easy to store and sterilize prior to use. Other advantages include non-thrombogenicity and a compliance which approximates that of natural blood vessels.

According to the method of the present invention, a tubular vascular prosthesis is formed by providing a sheet of tissue and a tubular support frame. The tissue is then attached to the tubular support frame to define a substantially unrestricted blood flow lumen therethrough. The tissue sheet may be obtained from the host or from other human or animal (non-autologous) sources. Typically, the tissue is trimmed into a shape to facilitate rolling onto the frame, usually a rectangular shape. The tissue will usually be pericardium, fascia, rectus sheath, venous tissue, or the like, and will preferably but not necessarily be treated with a cross-linking agent or other stabilizing agent (preservative) prior to formation.

The tubular support frame may have a variety of configurations. In a first embodiment, the tubular support frame includes at least an inner frame component and an outer frame component, where the attaching step comprises capturing the tissue sheet between the inner component and the outer frame component. The inner and outer frame components may be in the form of helices, longitudinally spaced-apart rings, or other conventional intravascular stent structures and the like. In a preferred aspect of the present invention, the inner and outer frame components comprise concentric mating structure which clamp the tissue therebetween without suturing. The frame thus supports the clamped tissue along the entire length of the graft to provide support and precise dimensional control.

Alternatively, the tubular support frame may include a single frame member having a plurality of fasteners disposed thereover. In such case, the attaching step comprises attaching the tissue to the fasteners, for example by penetrating the fasteners through the tissue. As yet another alternative, the tissue may be attached to a single frame using separate fasteners, such as staples which are penetrated through the tissue and into the frame. In yet another alternative, the attaching step may comprise disposing a sleeve over the tissue which in turn is disposed over the tubular frame.

Systems for forming tubular prostheses according to the present invention comprise a cutter and a tubular frame. The cutter is designed to trim the sheet of harvested tissue into a predetermined pattern, typically a rectangular pattern. The tubular frame is capable of supporting the tissue trimmed by the cutter and a tubular geometry having a substantially unrestricted flow lumen therethrough. Usually, a plurality of cutters and a plurality of tubular frames will be provided with matched pairs of cutters and frames used for forming tubular prostheses having different dimensions. The system may further include a mandrel for holding the tissue as the tissue is attached to the frame, and may still further include a cross-linking agent or other stabilizing agent or preservative for treating the tissue prior to attachment to the frame. The frame may comprise any of the structures described above.

In another aspect of the present invention, a tubular frame for supporting tissue in a tubular geometry with a substantially unrestricted flow lumen therethrough comprises a first tubular frame component having tissue attachment means thereon. The tubular frame typically has a diameter in the range from 1 m to 30 m, preferably from 3 mm to 25 mm, and a length in the range from 1 cm to 30 cm, preferably from 5 cm to 15 cm. The length will be determined at least in part by the length and amount of tissue available from an individual patient. In some cases, frames even longer than 30 cm might find use, but the resulting longer grafts will rarely be needed in some cases, the length of the tubular frame will be adjustable, for example by cutting a desired length of frame or frame components from a relatively long frame stock.

The frame will usually be composed of a resilient metal, and may comprise either a helical element or a plurality of longitudinally spaced-apart ring elements. Attachment means may comprise any one of a second tubular frame component configured to mate with the first tubular frame component, e.g., a pair of nesting helical frame elements, a plurality of fasteners disposed over the first tubular frame component, a sleeve which is received over the exterior of the first tubular frame component, staples for attaching the tissue to the frame component, or the like. Optionally, two or more frames or frame segments may be linked together to create longer grafts, with the frames or frame segments being interlocked and/or overlapped to create a continuous lumen through the resulting assembly.

DESCRIPTION OF THE SPECIFIC EMBODIMENTS

Figure 1:
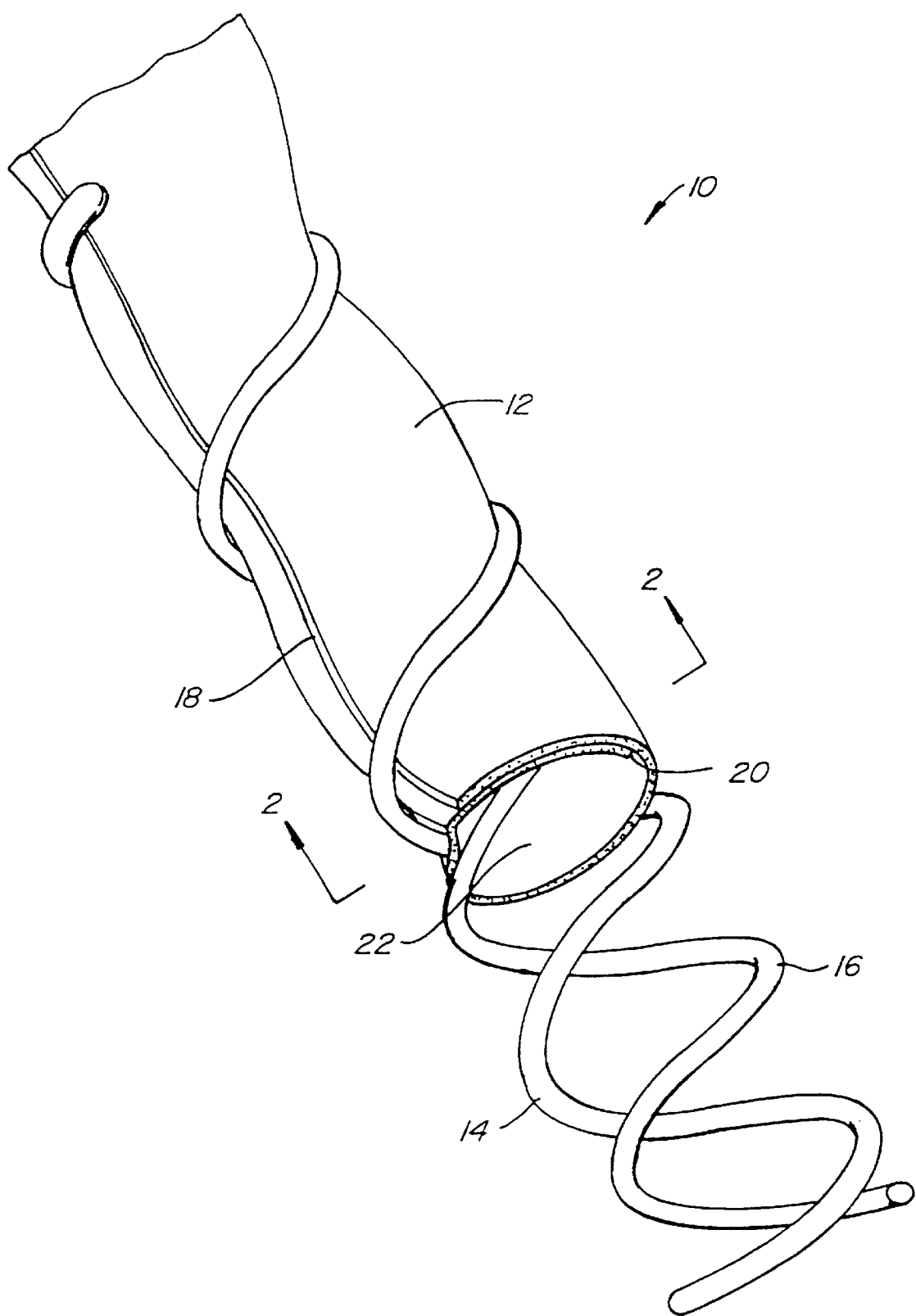
FIG. 1 is a perspective view of a vascular prostheses constructed in accordance with the principles of the present invention, shown with portions broken away.

The present invention provides vascular prostheses, also referred to as vascular grafts, intended for use in medical procedures requiring replacement or bypass of a patient's blood vessels. Most commonly, vascular prostheses will be used in peripheral vascular bypass, coronary artery bypass (CABG) procedures, but they also may find use in aneurysm repair; vascular access shunts; vessel reconstruction, such as pulmonary outflow tract and aortic outflow tract; as a conduit for valvular repair; and the like.

The tissue employed in the vascular prosthesis will be obtained from a human or other animal source, usually but not necessarily being obtained from the patient or host into which the prosthesis is to be implanted. The tissue may comprise any body tissue having sufficient strength and elasticity to act as the primary component of the prosthesis, usually being obtained from the pericardium or a fascial layer, such as the fascia lata. Other tissue sources include rectus sheath and venous tissues. The tissue will be harvested by conventional techniques, such as those described in Love, *Autologous Tissue Heart Valves*, R.G. Landes Co., Austin, Tex., 1993, Chapter 8.

Although not generally preferred, the present invention can be employed to strengthen conventionally harvested and prepared saphenous veins using any of the inner stent/outer stent combinations described below. The primary difference when using a saphenous vein tissue material source is that the tissue will not be rolled or layered over itself as will be the case with sheet-like tissue sources.

The amount of tissue harvested will depend on the size of the vascular prosthesis to be prepared. Typically, the sheet of tissue initially obtained will be generally rectangular, having a length in the range from about 5 cm to 35 cm, usually 5 cm to 15 cm for pericardium, and a width in the range from about 2 cm to 20 cm, usually about 2 cm to 5 cm for pericardium. After harvesting, the tissue will be trimmed to size, usually using a cutting die, stencil, or other pattern-forming device capable of trimming the tissue to the precise dimensions required. A presently preferred technique uses parallel, spaced-apart cutting blades (such as two circular, rolling blades attached to a single handle) which may be used to cut tissue having a precisely defined width. The particular dimensions, of course, will depend on the dimensions of the vascular prosthesis to be formed. Typically, the sheet will be cut into a rectangular pattern having a length and width in the ranges set forth above.

After harvesting but usually before trimming, the tissue will be treated by conventional methods to enhance its stability and durability. For example, the tissue may be briefly immersed in a cross-linking solution, such as glutaraldehyde, in order to fix the tissue. It has been found that glutaraldehyde-treated tissue remains antigenically compatible with the host from which it has been harvested. Suitable techniques for treating the harvested tissue with glutaraldehyde are described in Love, supra., Chapter 5.

While it is preferred that the tissue be obtained from the patient in which the vascular prosthesis is to be implanted (referred to as "autologous" tissue), it is also possible to obtain tissue from other human and animal sources. For example, tissue could be obtained from human cadavers, including frozen (cryo-preserved) cadaver tissue, treated with the cross-linking or other preserving agent, and then employed to make vascular prostheses according to the teachings herein. Tissue could also be obtained from non-human animal sources, such as bovine tissue, porcine tissue, and the like. It would also be possible to use luminal tissues, such as venous tissues, e.g., human and non-human saphenous veins. While a particular advantage of the present invention is it allows the use of non-luminal tissues to form vascular and other graft structures, the use of the frames of the present invention would also be advantageous in supporting saphenous vein grafts along their lengths. The saphenous or other veins can either be split longitudinally, and formed as described hereinafter for other flat tissue sources, or alternatively could be placed intact over an inner stent with a second stent or sheath then being placed over the exterior of the vein.

Preferably, the grafts of the present invention will be formed from a single piece of tissue having a length which is generally equal to the length of the graft and having a single overlap extending longitudinally down the length of the graft. Other graft constructions, however, will be possible. For example, a single long, relatively narrow strip of tissue could be wrapped spirally around the graft, thus having a spiral overlap extending down the length of the graft. As a further alternative, two or more tissue sections could be wrapped around the frame to form the graft of the present invention in a variety of geometries. While the preferred tissue geometry will be illustrated and described hereinafter, it is appreciated that the present invention is not so limited.

The tubular support frame of the vascular prosthesis will typically be composed of a non-biologic material having sufficient strength to maintain the rolled tissue in a tubular geometry with a substantially unrestricted lumen therethrough, but with sufficient flexibility to allow the prosthesis to be bent and with sufficient compliance to allow the prosthesis to accommodate pulsatile blood flow. Usually, the tubular support will be made from a spring metal, such as a spring stainless steel or a shape memory alloy in its superelastic state, such as a nickel-titanium alloy. Exemplary materials include alloy MP35N (Maryland Specialty Wire, Inc., Cockeysville, Md. 21030) and nickel titanium alloy SE508 (Nitinol Device and Component, Inc., Fremont, Calif.). The frame could also be formed from plastic materials having the requisite strength and flexibility requirements, such as thermoplastics. A third alternative would be thermoplastic covered metal wires. The use of both plastics and thermoplastic-covered wires is advantageous if the frame is trimmed prior to use since the plastic materials will reduce the formation of sharp edges on the frame. Thermoplastic frame materials can also permit sewing or suturing through the frame. Both metal and plastic frame components may optionally be covered with polyester (Dacron®) in order to enhance biocompatibility and non-immunogenicity.

The dimensions of the tubular support frame will define the dimensions of the vascular prosthesis. Typically, the support frame will have a diameter in the range from about 1 m to 30 m, usually from 3 mm to 25 mm, and a length in the range from 1 cm to 35 cm, usually from 1 cm to 25 cm, and may usually range from 5 cm to 15 cm. The rolled tissue supported by the frame will often extend slightly beyond the ends of the frame, typically by a distance in the range from 1 m to 10 mm, usually from 2 mm to 6 mm. Such tissue extensions can facilitate suturing of the prosthesis to form end-to-end and end-to-side anastomoses in performing CABG and other procedures.

The tubular support frame will usually include at least two components, such as an inner frame component and an outer frame component, as described in more detail below. Generally, however, at least one of the frame components will extend continuously from a proximal end of the graft to a distal end of the graft. It is possible, however, that the tubular support frame will include two or more separate, longitudinally-separated segments or components which may be unattached or attached by overlapping or by other non-permanent fastening. The use of multiple, longitudinal segments may be advantageous in enhancing flexibility and/or facilitating the design and fabrication of longer tubular grafts.

The tissue will be rolled into the desired tubular configuration and attached to the tubular support frame so that the tissue is maintained in its desired tubular geometry. Tissue attachment may be provided in a variety of ways. Preferably, the tissue will be attached to the frame without suturing or otherwise penetrating the sheet of tissue. In that way, integrity of the tissue is enhanced and leakage of blood or other fluids through the prostheses is reduced. In alternative embodiments, the tissue may be attached to the tubular support frame using penetrating attachment means, such as hooks, barbs, staples, or the like. Preferably, the tissue will not be sutured to the frame or otherwise to enhance closure of the tubular tissue structure. Usually, leakage from the tubular tissue structure will be prevented by overlapping the adjacent (rolled) edges of the tissue by an arc of at least 35°, usually being in the range from 45° to 720° or more, preferably being about 360° (i.e., twice-wrapped).

In the exemplary embodiment, the tissue will be overlapped by the requisite amount and will be held together by the tubular support frame, as described in detail hereinafter. In some cases, however, it may be further desirable to provide adhesives, such as fibrin glues, biological adhesives, synthetic glues (cyanoacrylates), or the like, to bond the overlapping layers. It may also be possible to provide laser welding of the tissue layers together, also to enhance the bonding. It would also be possible to suture the layers together, although this will generally be less preferred for the reasons set forth above in the Background section. It would further be possible when employing an adhesive to join the adjacent tissue edges together in an abutting fashion, forming an axially extending butt-joint, although this method is not presently preferred.

A preferred tubular support frame will comprise an inner frame component and an outer frame component, where the rolled sheet of tissue is captured between the inner and outer components. In a particularly preferred embodiment, both the inner and outer frame components are helical elements, usually having identical diameters and pitches. In the case of helical stents, it is possible that the helical turns will include a secondary serpentine or zig-zag pattern to improve the support for the tissue therebetween. The sheet of tissue is rolled over a first of the helical support elements, which acts as the inner support. The second helical component is then placed over the tissue, typically so that the outer helical support runs between the turns of the inner helical support. Other embodiments utilize longitudinally spaced-apart support rings or other structures, such as those conventionally used in vascular stents.

Figure 2:
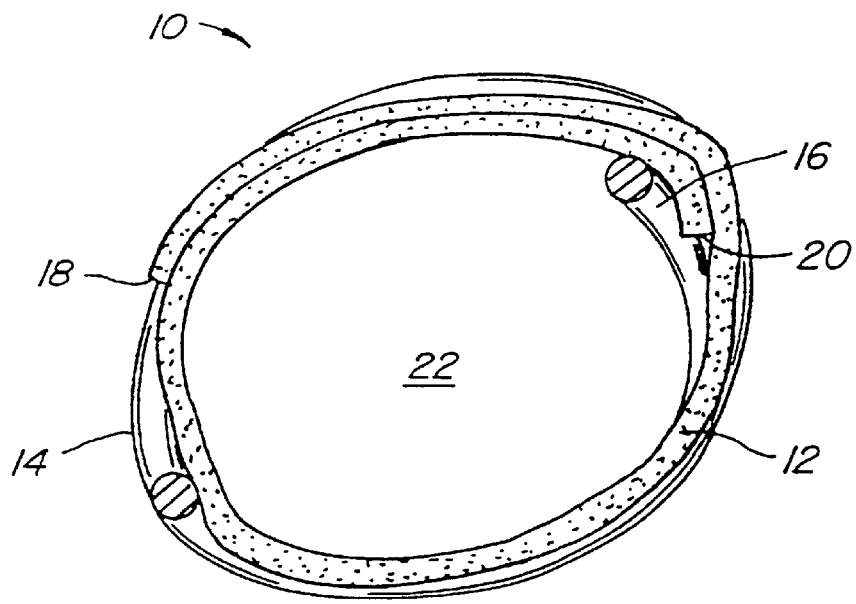
FIG. 2 is a cross-sectional view taken along line 2—2 of FIG. 1.
Figure 3:
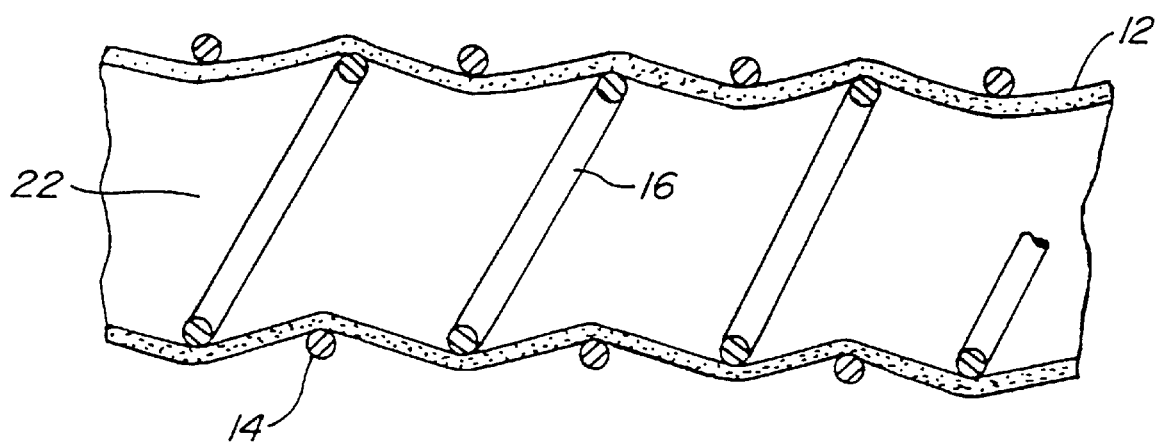
FIG. 3 is a partial, longitudinal cross-sectional view of the prostheses of FIG. 1.

Referring now to FIGS. 1–3, a vascular prosthesis 10 comprising a rolled sheet of tissue 12, an outer helical support element 14, and an inner helical support element 16, is illustrated. The tissue 12 is rolled from a rectangular sheet so that longitudinal edges 18 and 20 are parallel to each other and overlap by an arc in the range set forth above. Such overlapping will inhibit the leakage of blood or other body fluids which are being carried through lumen 22 of the graft 10.

The helical support elements 14 and 16 may have identical dimensions, i.e., diameter, length, and pitch. The diameter and length will be within the ranges set forth above, and the pitch, i.e., distance between successive turns of the helix, will usually be in the range from 1 m to 10 mm, usually being from 1 m to 6 mm, and preferably being from about 2 mm to 4 mm. It is desirable to increase the pitch as much as possible, while maintaining sufficient capture of the tissue therebetween to prevent leakage of fluent from the prosthesis. Thus, it will frequently be possible to increase the pitch of the helical support elements 14 and 16 by also increasing the amount of overlap between the parallel edges 18 and 20. In some cases, it may be preferred to have the outer stent formed from slightly larger diameter wire than is the inner stent, e.g. 0.007 in and 0.0057 in., respectively. The outer stent may also have a slightly larger diameter than the inner stent by-about one wire diameter, e.g. 0.005 in.

Figure 4:
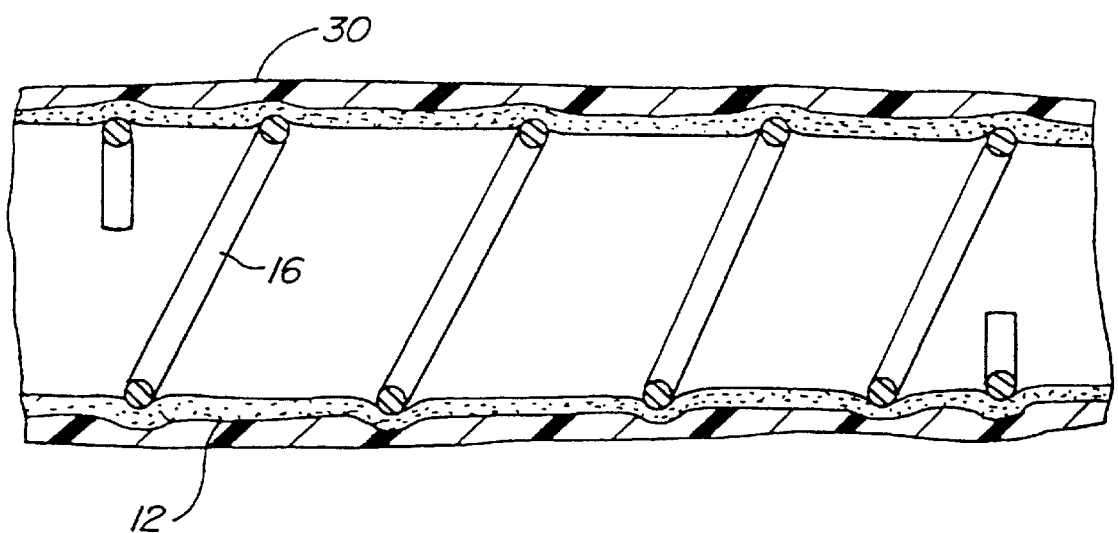
FIG. 4 is a partial cross-sectional view of an alternative embodiment of the prosthesis of the present invention.
Figure 5:
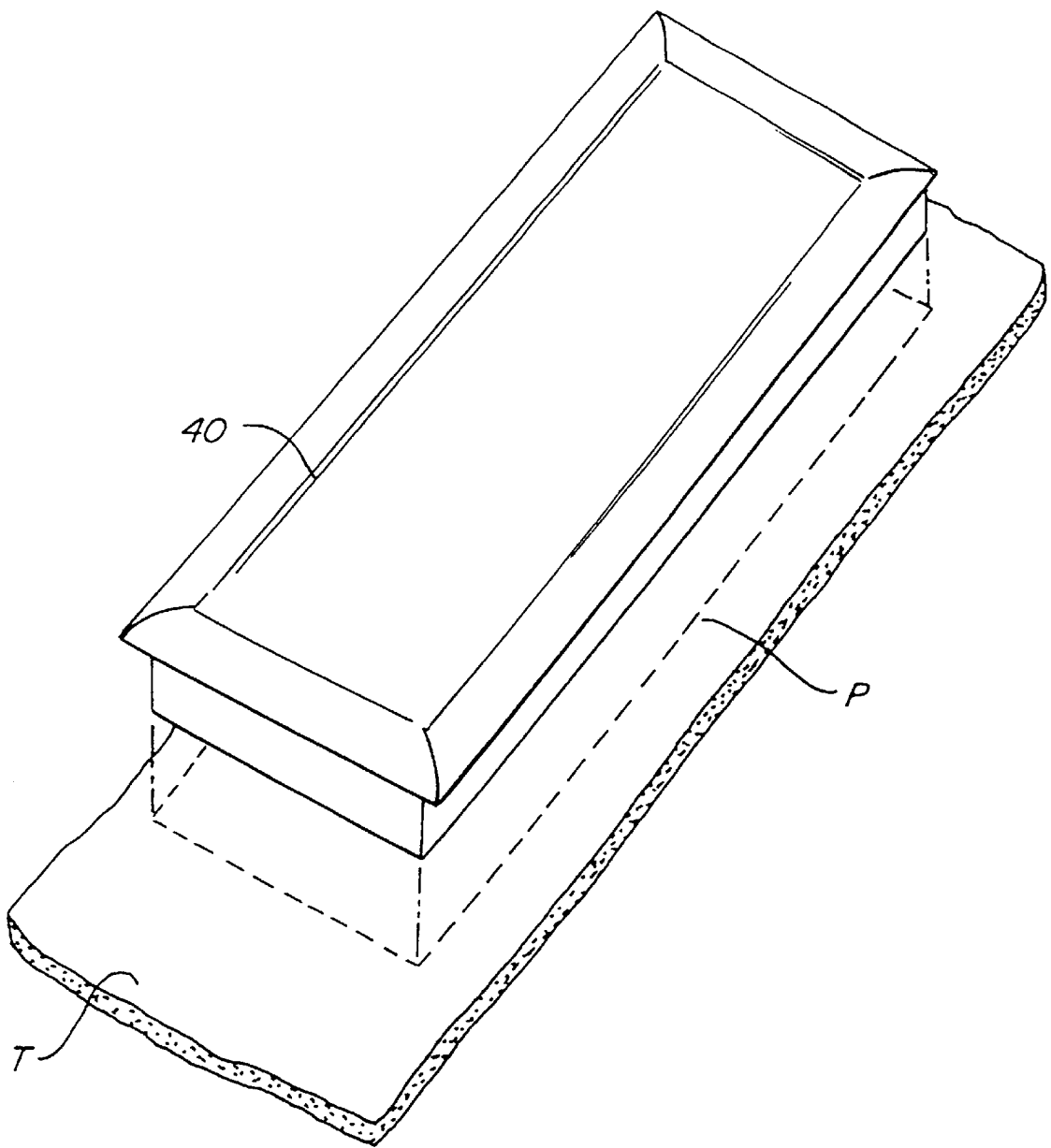
FIGS. 5–8 illustrate a method for preparing the vascular prosthesis of FIG. 1.

As an alternative to employing the outer helical support element 14, an outer sleeve 30 may be placed over the tissue layer 12, as illustrated in FIG. 4. The inner helical support element 16, and other features of the graft, may be identical to those of the vascular prosthesis 10 of FIGS. 1–3. Use of an outer sleeve may have certain advantages. For example, use of an elastic material may facilitate placement of the sleeve over the tissue and underlying frame component. Porous membrane materials may also be employed in the sleeve in order to enhance tissue ingrowth. Finally, the use of elastic sleeve materials may enhance the compliance of the tubular prosthesis.

In some cases, use of a sleeve 30 could obviate the need for the internal stent 16. For example, the tissue layer 12 could be glued, welded (e.g. using laser energy), sutured, or otherwise attached to the sleeve 30 so that the sleeve provides complete support for the tissue. Typically, the tissue layer could be laminated to the sleeve material 30 in a generally flat configuration, and the laminated structure rolled to form the vascular prothesis.

As a still further alternative, the inner stent 16 (in any of the embodiments) could be formed from a biodegradable material that erodes, typically over at least one week and usually over several weeks or months. Suitable erodible materials are composed of at least one polymer system selected from the group consisting of lactic acid/glycolic copolymer, carbophenoxy propane/sebacic acid, polycaprolactones, polyanhydride and poly ortho-esters.

It is also possible that the inner stent will be removable. The purpose of erodible and/or removable inner stents will be to avoid possible obstructions on the inner surface of the lumen created by the graft. The surface irregularities formed by the inner lumen in some cases could act as a site for thrombus formation, although it is presently believed that it will not be necessary to remove the inner stent.

Referring now to FIGS. 5–8, a method for preparing the vascular prosthesis 10 of FIGS. 1–3 will be described. A sheet of tissue T is harvested from the patient or other animal source, as described previously. The sheet will usually be treated with glutaraldehyde or other fixative or cross-linking agent, as also described previously. It is desirable that the tissue be treated prior to trimming since treatment can cause a slight shrinkage. The tissue sheet T will then be trimmed, preferably using a cutter 40 or similar device capable of cutting the tissue into a rectangular pattern P, as shown on the tissue in broken line.

Figure 6:
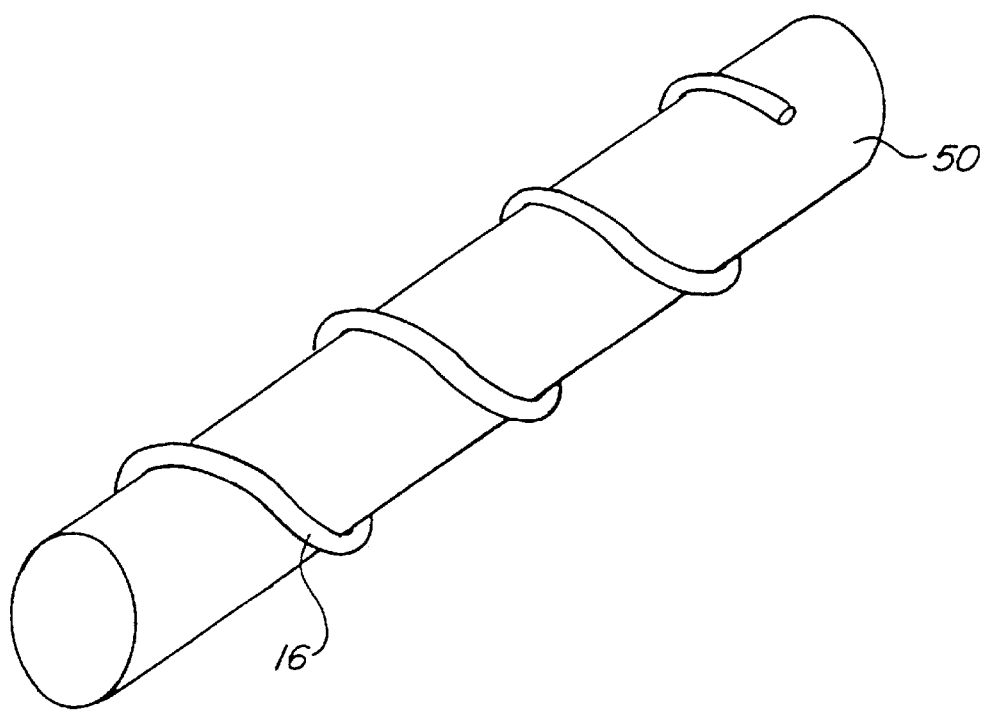
Figure 7:
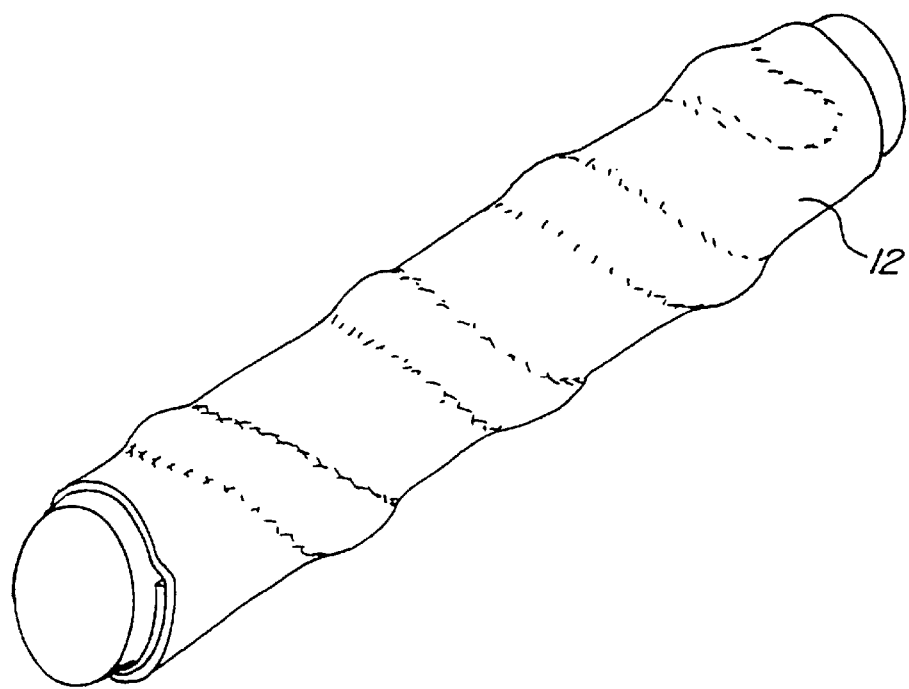
Figure 8:
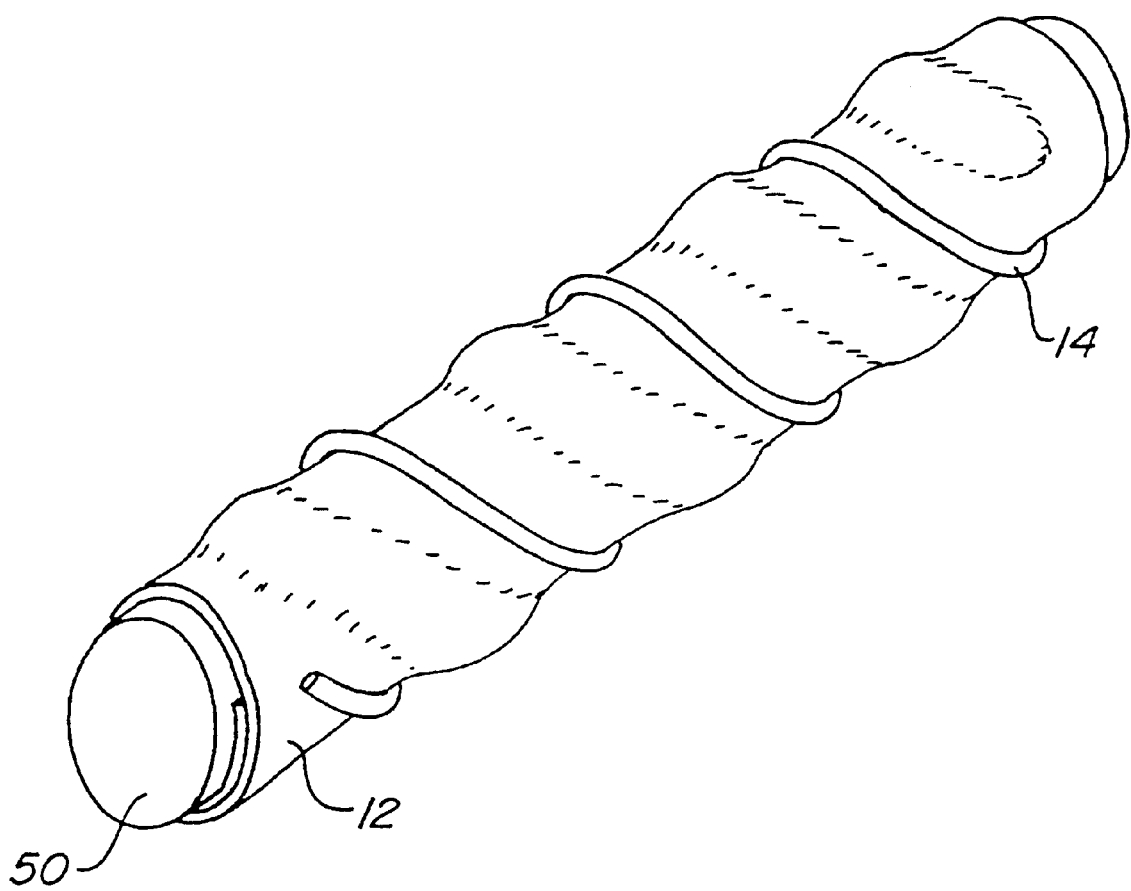

The inner helical support element 16 is typically placed over a mandrel 50, as shown in FIG. 6. The trimmed sheet of tissue 12 is then rolled over the mandrel, as shown in FIG. 7. The outer helical support element 14 may then be placed over the tissue 12, typically by expanding the diameter of the helix and, after properly positioning over the tissue 12, allowing the helix to contract onto the tubular form of the tissue, as shown in FIG. 8. The mandrel 50 is then removed. The prosthesis 10 is then ready to be used in a conventional vascular bypass or replacement procedure. Optionally, the outer helical support element may be applied by screwing the helices together or by winding the coils of the outer helical support element over the tissue wrapped over the inner helical support element 16 and mandrel 50.

Figure 9:
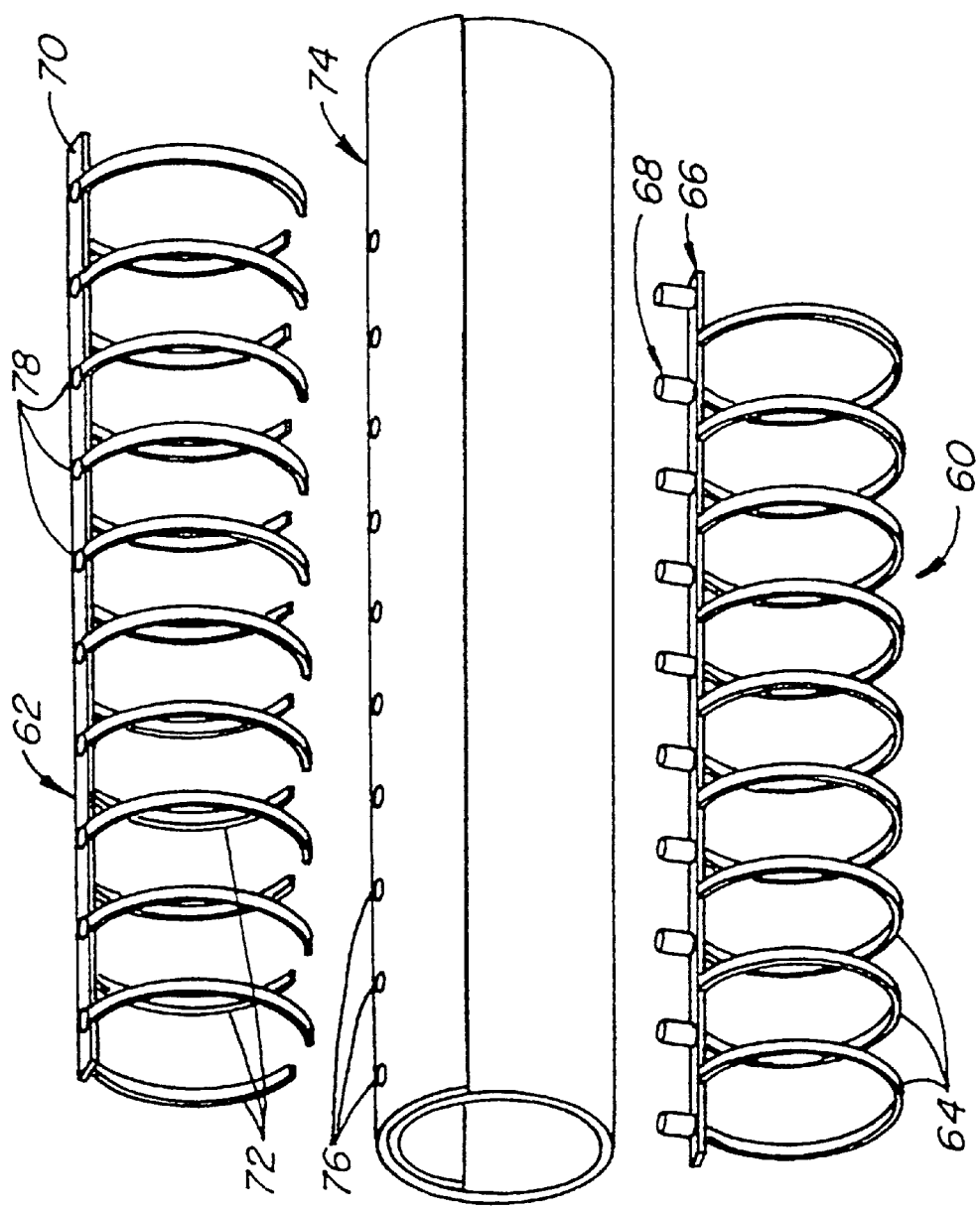
FIG. 9 illustrates an alternative construction of a vascular prostheses constructed in accordance with the principles of the present invention, shown in an exploded view.

Referring to FIG. 9, an alternative embodiment of the vascular prosthesis of the present invention will be described. The prosthesis comprises a tubular support frame including an inner frame member 60 and an outer frame member 62. The inner frame member 60 includes a plurality of ring elements 64 which are longitudinally spaced-apart along a longitudinal spine 66. A plurality of pins 68 are disposed along the upper surface of the spine 66 and are disposed in a radially outward direction. The outer frame member 62 also comprises a longitudinal spine 70 and includes a plurality of ring elements 72 longitudinally spaced-apart on the spine. The ring elements 72 are open so that each ring forms a C-clamp. Tissue 74 is rolled over the inner frame member 60, with a plurality of apertures 76 formed to receive the pins 68. The outer frame member 70 is then placed over the rolled tissue 74, with apertures 78 and the spine 70 also being received over pins 68. The rings 72 are spaced so that they are received between each of the rings 64 in the inner frame member 60.

Figure 10:
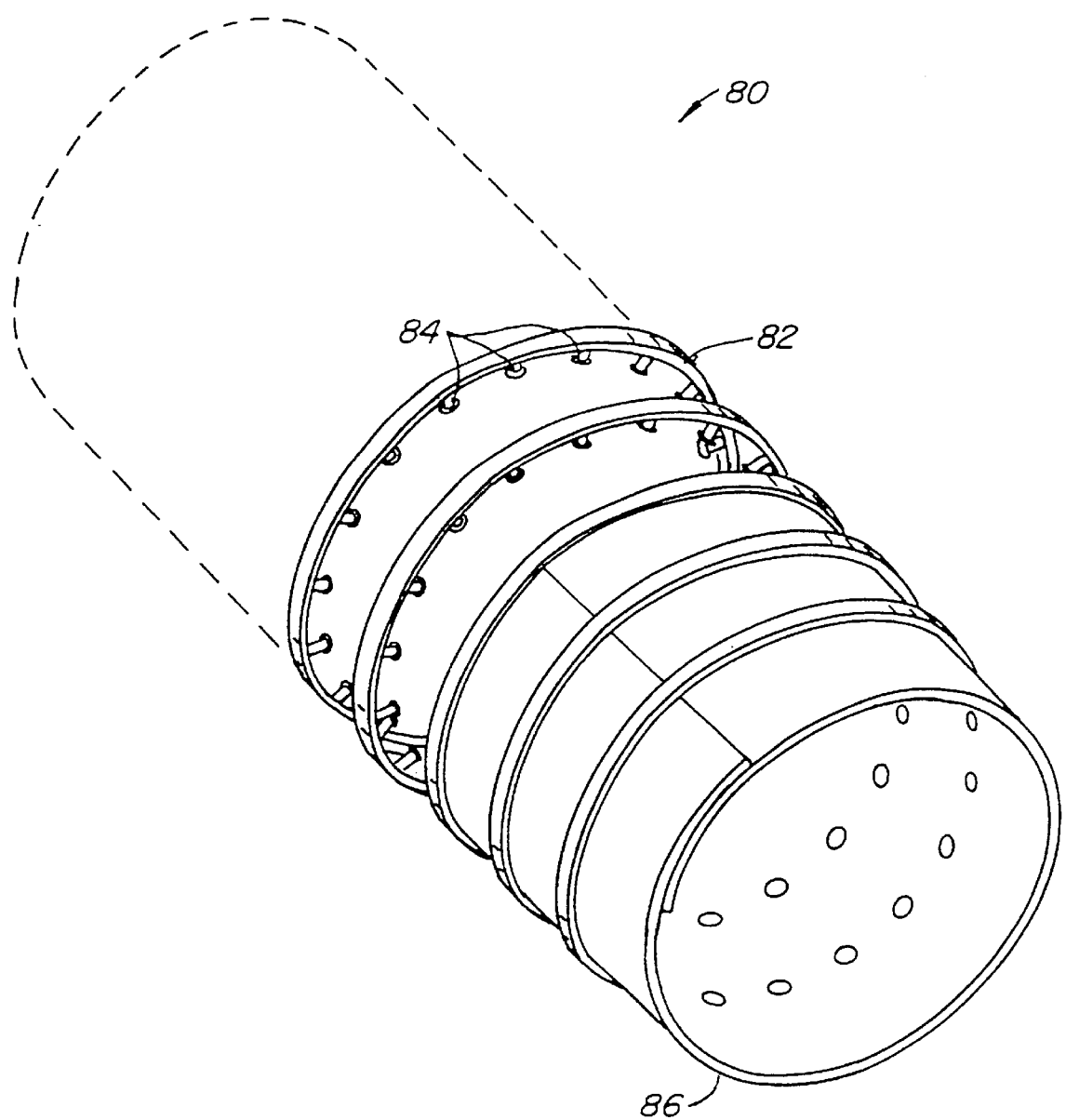
FIG. 10 illustrates yet another alternative environment of a vascular prosthesis constructed in accordance with the principles of the present invention.

Another vascular prosthesis 80 is illustrated in FIG. 10. Prosthesis 80 comprises a plurality of independent ring elements 82, each of which includes a plurality of "mushroom" fasteners disposed about its inner periphery. The fasteners 84 project radially inward so that a rolled tissue can be pressed onto the fasteners 84, as illustrated. Optionally, the tissue could be perforated prior to placement over the ring elements 82 to facilitate placement over the fasteners 84. It would also be possible to connect the ring members 82 with one or more longitudinal members if it is desired to increase the column strength.

Figure 11:
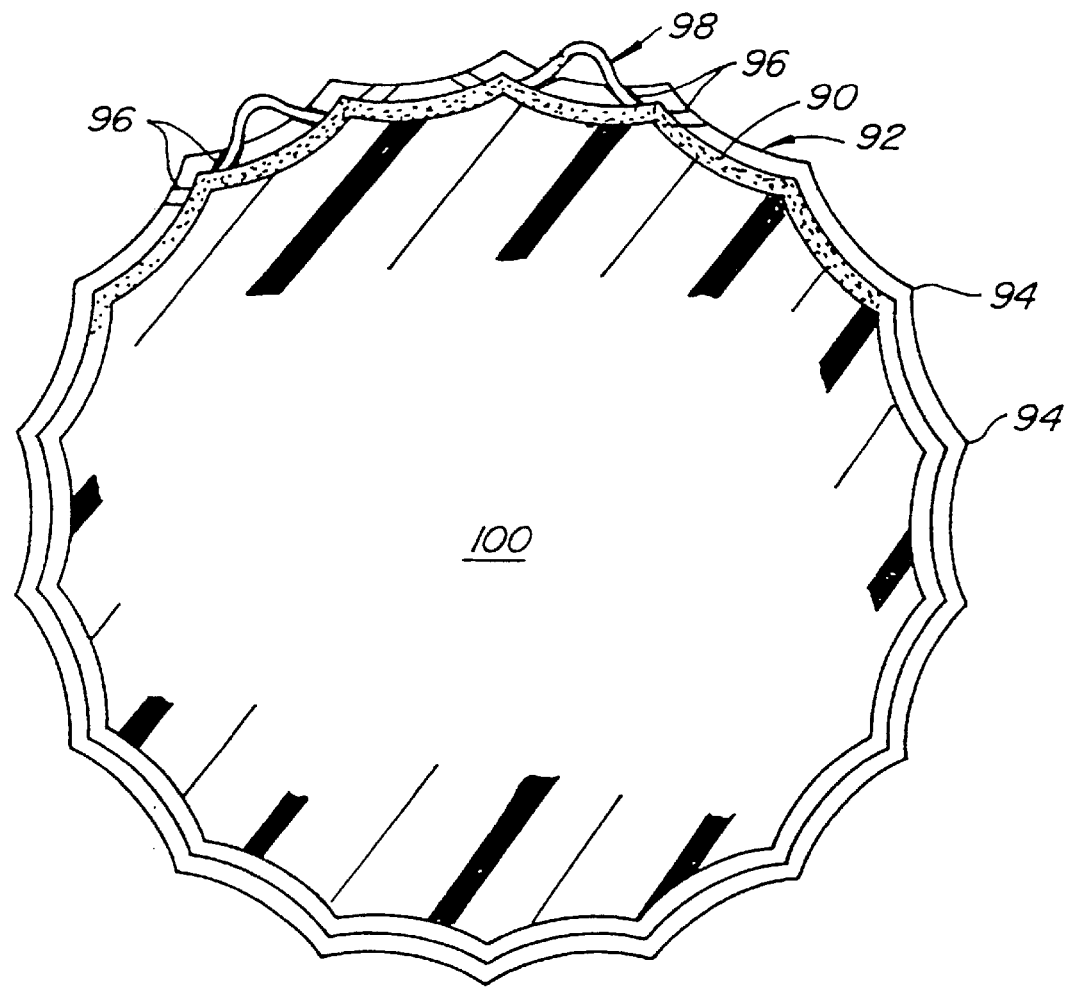
FIGS. 11 and 12 illustrate another method for attaching tissue to a tubular frame member according to the method of the present invention.
Figure 12:
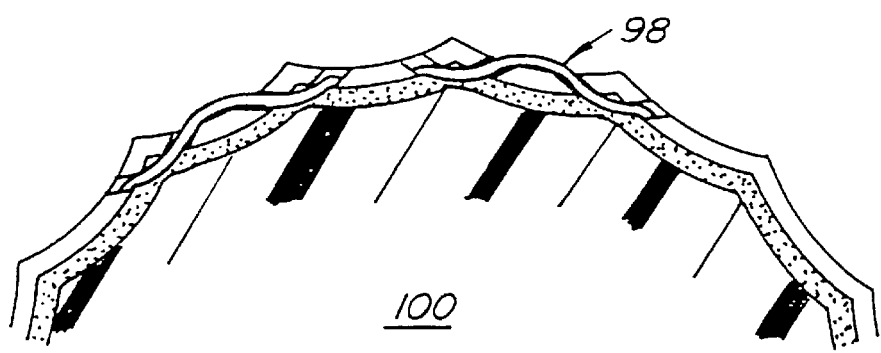

A further alternative approach for attaching a tissue layer 90 to a supporting ring element 92 is illustrated in FIGS. 11 and 12. The tissue 90 is placed over a mandrel having a cross-sectional shape which matches that of the ring element 92. The ring element 92 includes a plurality of peaks 94, each of which includes a pair of channels 96 therein. The channels 96 are aligned so that staples 98 may be inserted therethrough, allowing stapling of the ring element 92 to the tissue, as shown in FIG. 12. The supporting mandrel 100 is shaped to conform to the ring elements 92.

Although the foregoing invention has been described in some detail by way of illustration and example, for purposes of clarity of understanding, it will be obvious that certain changes and modifications may be practiced within the scope of the appended claims.

What is claimed is:

1. A tubular frame for supporting tissue in a tubular geometry with a substantially unrestricted lumen therethrough, said frame comprising a first tubular frame component comprising a first helical wire support element and a second tubular frame component comprising a second helical wire support element, wherein the first helical wire support element and the second helical wire support element have the same length and pitch and wherein the second helical wire support element has a diameter which is equal to or larger than the diameter of the first tubular frame component by no more than a wire diameter of the second helical wire support element, wherein said first and second tubular frame components are separate from each other and may be disposed over an inner surface and an outer surface, respectively, of a tubular tissue structure to form a vascular prosthesis by clamping the tissue therebetween without suturing.

2. A tubular frame as in claim 1, wherein the first and second tubular frame components each have a diameter in the range from 1 mm to 30 mm and a length in the range from 1 cm to 30 cm.

3. A tubular frame as in claim 2, wherein each tubular frame component has a pitch in the range from 1 mm to 10 mm.

4. A tubular frame as in claim 1, wherein each helical wire support element is composed of a resilient metal.

* * * * *